US006409695B1

(12) United States Patent
Connelly

(10) Patent No.: US 6,409,695 B1
(45) Date of Patent: Jun. 25, 2002

(54) ANKLE-FOOT ORTHOTIC

(76) Inventor: John D. Connelly, 3155 Werkridge Dr., Cincinnati, OH (US) 45248

( * ) Notice: Subject to any disclaimer, the term of this patent is extended or adjusted under 35 U.S.C. 154(b) by 0 days.

(21) Appl. No.: 09/362,274

(22) Filed: Jul. 27, 1999

(51) Int. Cl.[7] ................................................. A61F 5/00
(52) U.S. Cl. ........................................... 602/27; 602/16
(58) Field of Search ............................... 602/5, 16, 26, 602/23, 27–29, 21; 403/59, 114, 115, 220; 16/224; 623/27, 35; 188/268; 267/150, 141.1, 141.2, 141.4; 74/470; 248/562, 564, 566–570; 128/882

(56) References Cited

U.S. PATENT DOCUMENTS

| 816,866 A | * | 4/1906 | Leonard ...................... 623/35 |
| 1,159,473 A | * | 11/1915 | Church |
| 3,316,558 A | * | 5/1967 | Mortensen |
| 3,805,773 A | * | 4/1974 | Sichau ...................... 128/80 E |
| 4,038,705 A | * | 8/1977 | Owens et al. ...................... 3/2 |
| 4,289,122 A | * | 9/1981 | Mason et al. .............. 128/80 E |
| 4,463,751 A | * | 8/1984 | Bledsoe ...................... 128/80 C |
| 4,472,079 A | * | 9/1984 | Langner ................... 403/59 X |
| 4,510,927 A | * | 4/1985 | Peters ...................... 128/80 H |
| 4,517,968 A | * | 5/1985 | Greene et al. ............ 128/80 H |
| 4,523,585 A | * | 6/1985 | Lamb et al. .............. 128/80 C |

(List continued on next page.)

OTHER PUBLICATIONS

Sharon Lisa Ye, *The Testing and Analysis of a Mechanical Joint For a Plastic Molded Ankle–Foot Orthotic*, pp. 1–27, University of Cincinnati, Master of Science Thesis, presented Aug. 7, 1998.*

*Primary Examiner*—Denise Pothier
(74) *Attorney, Agent, or Firm*—Michael C. Connelly

(57) ABSTRACT

An ankle-foot orthotic which permits plantarflexion and dorsiflexion while restricting inversion and eversion of the ankle. The orthotic includes a lower leg shell attachable to the lower leg of the wearer inside of the wearers trousers, a foot shell held in place inside the wearer's shoe, by the shoe itself, and a pair of mechanical joints attaching the lower leg shell to the foot shell. The mechanical joints are pivotally attached to the foot shell allowing rotation on an axis through the ankle joint, but are rigid perpendicular to the axis of the ankle joint thereby restricting sideways bending movement of the ankle. The mechanical joints have internal springs which allow translational movement of the lower leg shell relative to the foot shell providing greater comfort to the wearer by reducing rubbing and chafing of the user's leg while creating extra cushioning and shock absorption.

6 Claims, 4 Drawing Sheets

U.S. PATENT DOCUMENTS

| | | | |
|---|---|---|---|
| 4,655,201 A | * 4/1987 | Pirmantgen | 128/80 C |
| 4,665,904 A | * 5/1987 | Lerman | 128/80 H |
| 4,677,971 A | * 7/1987 | Lindemann | 602/21 |
| 4,719,926 A | * 1/1988 | Nelson | 128/80 H |
| 4,723,539 A | * 2/1988 | Townsend | 128/80 C |
| 4,738,252 A | * 4/1988 | Friddle et al. | 128/80 H |
| 4,771,768 A | * 9/1988 | Crispin | 128/88 |
| 4,881,532 A | * 11/1989 | Borig et al. | 128/80 A |
| 4,936,295 A | * 6/1990 | Crane | 128/80 H |
| 4,938,206 A | * 7/1990 | Harris et al. | 128/80 F |
| 4,938,777 A | * 7/1990 | Mason | 602/27 |
| 5,018,514 A | * 5/1991 | Grood et al. | 128/80 |
| 5,056,509 A | * 10/1991 | Swearington | 128/80 H |
| 5,069,202 A | * 12/1991 | Prock | 128/80 H |
| 5,086,760 A | * 2/1992 | Neumann et al. | 602/27 |
| 5,094,232 A | * 3/1992 | Harris et al. | 602/16 |
| 5,209,722 A | * 5/1993 | Miklaus et al. | 602/27 |
| 5,242,379 A | * 9/1993 | Harris et al. | 602/27 |
| 5,257,680 A | * 11/1993 | Corcoran et al. | 188/129 |
| 5,328,444 A | * 7/1994 | Whiteside | 602/16 |
| 5,348,532 A | * 9/1994 | Prahl | 602/24 |
| 5,352,190 A | * 10/1994 | Fischer et al. | 602/23 X |
| 5,368,551 A | * 11/1994 | Zuckerman | 602/23 |
| 5,429,588 A | * 7/1995 | Young et al. | 602/27 |
| 5,454,173 A | * 10/1995 | Falguere et al. | 36/117 |
| 5,472,410 A | * 12/1995 | Hamersly | 602/16 |
| 5,496,263 A | * 3/1996 | Fuller, II et al. | 602/27 |
| 5,542,774 A | * 8/1996 | Hoy | 403/116 |
| 5,676,642 A | * 10/1997 | Peters | 602/27 |
| 5,683,353 A | * 11/1997 | Hamersly | 602/16 |
| 5,716,335 A | * 2/1998 | Iglesias | 602/27 |
| 5,792,087 A | * 8/1998 | Pringle | 602/27 |
| 5,961,556 A | * 10/1999 | Thorn | 623/27 |

* cited by examiner

ANKLE-FOOT ORTHOTIC

BACKGROUND

The invention relates to orthotic braces and more particularly to pivotal leg and foot orthotics designed to permit plantarflexion and dorsiflexion while at the same time restricting inversion and eversion of the foot.

Due to the growth in popularity of sports participation there has been a subsequent growth in sports injuries, among them are ankle sprains and strains caused by excessive inversion or eversion of the foot. Those who suffer from such ankle injuries need an ankle brace which will allow them to rehabilitate the ankle by restricting the turning in and turning out, known as inversion and eversion, of the ankle but will allow free movement up and down of the ankle, known as dorsiflexion and plantarflexion. Such a brace needs to allow a user to continue walking or continue participating in athletic activity, if desired, and offer someone with weak ankles extra support. In short, a brace is needed which permits rotational movement through the axis of the ankle joint while restricting sideways bending movement perpendicular to the axis of the ankle joint. Such brace should also provide shock absorption and be comfortable, lightweight, unobtrusive, simple and inexpensive.

In the past such purposes have been achieved through the use of plastic or cloth foot and ankle members connected with a pivot joint, which allow rotational movement and restrict lateral movement but have little in the way of shock absorption and could allow rubbing and chafing of the lower leg if the leg is not properly wrapped. Such braces are often only wearable outside of the shoe and trousers, or cannot be worn with shoes or normal trousers at all, causing embarrassment and inconvenience to the wearer.

Additional braces allow for greater shock absorption and comfort, but in doing so, have complicated mechanisms joining foot and ankle members that are intricate, bulky and can be binding. Such braces are worn outside of the shoe and trousers or cannot be worn at all with shoes and trousers, again leading to embarrassment and inconvenience as the braces mentioned previously. Increased comfort has been achieved through greater flexibility laterally at the ankle joint, but this is not desirable when inversion and eversion are to be restricted. The joining mechanisms, being complicated, are more difficult to manufacture and therefore more expensive and more difficult to maintain.

Other braces attach directly to the wearer's shoe. These are not concealable, could damage the shoe they are affixed to and depend for strength, in part, on the shoe itself. The jointing mechanisms are also delicate, binding and pinching to material near the jointing mechanism.

Postoperative and post-injury braces are available which restrict inversion and eversion. These braces can have adjustments to allow some rotation of the ankle joint, but rotation is limited to a degree if not restricted altogether. Such braces are very bulky, heavy, unsightly and will allow only restricted plantarflexion and dorsiflexion of the foot. Such braces are not particularly designed for the purposes outlined above.

There is, thus a need for an ankle foot orthotic that is lightweight, strong, wearable inside of the shoe and trousers, simple to construct, use and maintain, comfortable and economical while at the same time permitting dorsiflexion and plantarflexion, restricting inversion and eversion of the foot and also providing a means of shock absorbency for the further comfort of an injured or healthy wearer participating in athletic activity, walking or rehabilitating.

SUMMARY

The present invention is directed to an ankle-foot orthotic that is lightweight, strong, wearable inside of the shoe and trousers, simple to construct, use and maintain, comfortable and economical while at the same time permitting dorsiflexion and plantarflexion, restricting inversion and eversion of the foot and also providing a means of shock absorbency for the further comfort of an injured or healthy wearer participating in athletic activity, walking or rehabilitating.

An ankle-foot orthotic having features of the present invention comprises a foot shell and a lower leg shell. The foot shell is pivotally attached to the lower leg shell employing a hinging means which permits rotational and translational movement of the foot shell relative to the lower leg shell. The hinging means also restricts sideways bending movement of the foot shell relative to the lower leg shell. The permitting of rotational movement allows desired dorsiflexion and plantarflexion of the foot to occur. Permitting translational movement allows up and down movement of the lower leg brace relative to the foot brace and provides shock absorbency to the orthotic and comfort for the wearer. The restriction of sideways movement prevents undesirable and injury causing excessive inversion and eversion of the foot.

The hinging means comprises a lateral mechanical joint located at the outside of the wearer's ankle and a medial mechanical joint located at the inside of the wearer's ankle. Each mechanical joint comprises a housing, a slider, a cover, a spring means and a pivoting means. The housing is hollow with an open face and a partially open end. The slider is positioned freely inside of the hollow cavity of the housing and is shaped to project through the partially open end of the housing but shaped not to be removable through the partially open end. A cover is affixed over the open face of the housing that in one embodiment of the invention is secured to the housing with screws. With the cover in place, the slider is rigidly held inside of the housing, thereby allowing only restricted side to side movement of the hinging means perpendicular to the ankle joint. Spring means are positioned inside of the housing which provide cushioning during translational movement of the slider, and the ankle-foot orthotic as well, while also allowing the slider and ankle-foot orthotic to return to a neutral position when neither upward or downward forces are being applied to the wearer's foot or leg. A pivoting means is attached to the end of the slider projecting through the partially open end of the housing thereby providing rotational movement to the ankle-foot orthotic.

The foot shell of the present invention is made of a plastic material that is molded in a thin layer to a wearer's foot so that the foot, with foot shell attached, can easily fit within the wearer's shoe. The foot shell comprises a lower plate on which the sole of the foot rests, an upright lateral sidewall adjacent to the outside of the foot and extending upward to the axis of the ankle joint where it flares away from the ankle to accept the fitting of the pivoting means, an upright medial sidewall adjacent to the inside of the foot and also extending upward to the axis of the ankle joint where it flares away from the ankle to accept the fitting of the pivoting means, and a rounded posterior wall in which the heel of the wearer is enclosed. The lower leg shell is likewise made of a plastic that is molded in a thin layer to a wearer's lower leg from slightly above the ankle joint to below the knee so that the lower leg, with leg shell attached, can easily fit within the trouser leg of the wearer. The lower leg shell comprises a vertical lateral sidewall adjacent to the outside of the leg having a top and a bottom end, the bottom end being flared away from the leg to accept attachment of the hinging means, a vertical medial sidewall adjacent to the inside of the leg having a top and a bottom end, the bottom end being flared to accept attachment of the hinging means, a vertical rounded posterior wall having a top end and a bottom end adjacent to the rear of the leg and hooked fabric attachment material adhered to the top end of the lower leg shell to secure the lower leg shell to the wearer's leg.

The lateral mechanical joint is fixedly attached to the flared bottom end of the vertical lateral sidewall of the lower leg brace with screws and pivotally attached to the flared upright lateral sidewall of the foot shell. The medial mechanical joint is fixedly attached to the flared bottom end of the vertical medial sidewall of the lower leg brace with screws and pivotally attached to the flared upright medial sidewall of the foot shell. In this way, both rotational movement and translational movement are provided to the foot-ankle orthotic while sideways bending movement is restricted.

The pivoting means of the present invention is comprised of a bolt which passes through a hole defined through the end of the slider that projects out of the partially open side of the hinging means housing, and passes through the upright lateral or upright medial sidewall of the foot shell. A retaining nut, threaded onto the end of the bolt secures the slider to the foot shell and thereby allows rotational movement.

The spring means of the present invention is comprised of elastic rubber material that is placed above and below the end of slider that is positioned inside of the housing. When translational, upwards or downwards, movement of the slider occurs perpendicular to the axis of the ankle joint, depending on the force applied, then a return to a neutral position is facilitated by the elastic rubber material when the force causing the movement is removed. In this manner shock to the foot and ankle is absorbed by the foot-ankle orthotic. Wearer comfort is also aided, as rubbing of the leg by the orthotic is decreased, since the upper shell can move translationally with the leg instead of remaining stationary and scraping the lower leg.

BRIEF DESCRIPTION OF THE DRAWINGS

These and other features, aspects, and advantages of the present invention will become better understood with regard to the following description and accompanying drawings where.

DESCRIPTION

Figure 1:
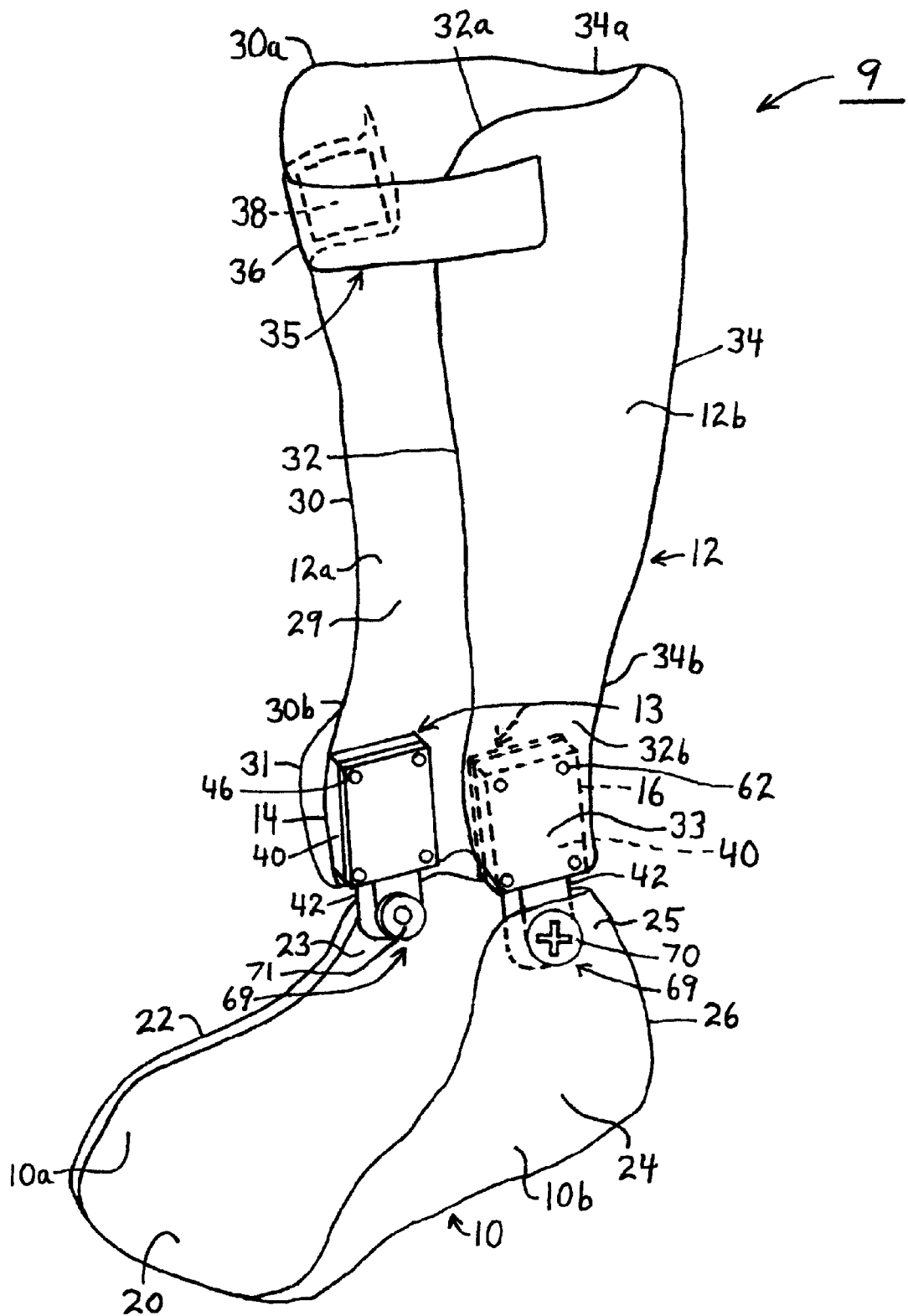
FIG. 1 is a frontal perspective of the ankle-foot orthotic.

Referring to FIG. 1, an ankle-foot orthotic 9 constructed in accordance with the invention comprises a foot shell 10, a lower leg shell 12 and a hinging means 13 pivotally connecting the foot shell 10 to the lower leg shell 12.

The foot shell 10, which is molded to the shape of a specific wearer's foot, employing a moldable plastic material which creates a thin walled casing defining an internal surface 10a and an external surface 10b, is comprised of a lower plate 20, an upright lateral sidewall 22, an upright medial sidewall 24 and rounded posterior wall 26. The sole of the wearer's foot rests upon and is supported by the lower plate 20 while the heel of the foot is held by the rounded posterior wall 26 which extends upward from the lower plate 20 adjacent to and integral with both the upright lateral sidewall 22 and the upright medial sidewall 24. The upright lateral sidewall 22 extends upward from the lower plate 20 on the outside of, and adjacent to the wearer's foot and ankle and terminates with a lateral flare 23 outward and away from the ankle, to allow clearance for the outside ankle bone and the slider 42 of the lateral mechanical joint 14, at the axis of the ankle joint. The upright medial sidewall 24 extends upward from the lower plate 20 on the inside of, and adjacent to the wearer's foot and ankle and terminates with a medial flare 25 outward and away from the ankle, to allow clearance for the inside ankle bone and the slider 42 of the medial mechanical joint 16 at the axis of the ankle joint. The foot shell 10 thereby forms a casing to hold the foot and is designed to be worn snugly on a stockinged or bare foot inside of a shoe and be secured to the foot by the shoe itself. The foot shell 10 may also be trimmed or custom shaped for the comfort of the wearer.

The lower leg shell 12, which is molded to the shape of a specific wearer's lower leg, employing a moldable plastic material which creates a thin walled casing defining an inner surface 12a and an outer surface 12b, is comprised of a vertical lateral sidewall 30, a vertical medial sidewall 32, a vertical rounded posterior wall 34 and a means to secure 35 the lower leg shell 12 to the wearer's leg. The lower leg shell 12 is molded to the shape of the wearer's leg from just above the ankle to below the knee and has a gap 29, opposite the vertical rounded posterior wall 34, to allow insertion of the lower leg into the lower leg shell 12. The vertical lateral sidewall 30 is adjacent to, and molded to the shape of the outside surface of the wearer's lower leg. The vertical lateral sidewall 30 has a lateral top end 30a and a lateral bottom end 30b. The lateral bottom end 30b terminates with a lateral splay 31 outward and away from the outside of the leg, permitting clearance for the housing 40 of the lateral mechanical joint 14. The vertical medial sidewall 32 is adjacent to, and molded to the shape of the inside surface of the wearer's lower leg. The vertical medial sidewall 32 has a medial top end 32a and a medial bottom end 32b. The medial bottom end 32b terminates with a medial splay 33 outward and away from the inside of the leg, permitting clearance for the housing 40 of the medial mechanical joint 16. The rounded posterior sidewall 34 is adjacent to, and molded to the shape of the rear surface of the wearer's lower leg. The rounded posterior sidewall 34 has a posterior top end 34a and a posterior bottom end 34b and is adjacent to and integral with the vertical lateral sidewall 30 and the vertical medial sidewall 32. The lower leg shell 12 thereby forms a casing to hold the lower leg and is designed to be worn snugly on a stockinged or a bare lower leg inside the trousers of the wearer. A means to secure 35 the lower leg shell 12 to the leg is provided by a square of hooked fabric attachment material 38 adhered near the lateral top end 30*a* of the vertical lateral sidewall 30 and a strip of hooked fabric attachment material 36 fastened near the medial top end 32*a* of the vertical medial sidewall 32. The strip of hooked fabric attachment material 36 is of sufficient length to reach across the gap 29 to the square of hooked fabric attachment material 38 and hook thereon, and subsequently secure the lower leg shell 12 to the leg. The lower leg shell 12, as the foot shell 10, may be trimmed or custom shaped for the comfort of the wearer.

Figure 2:
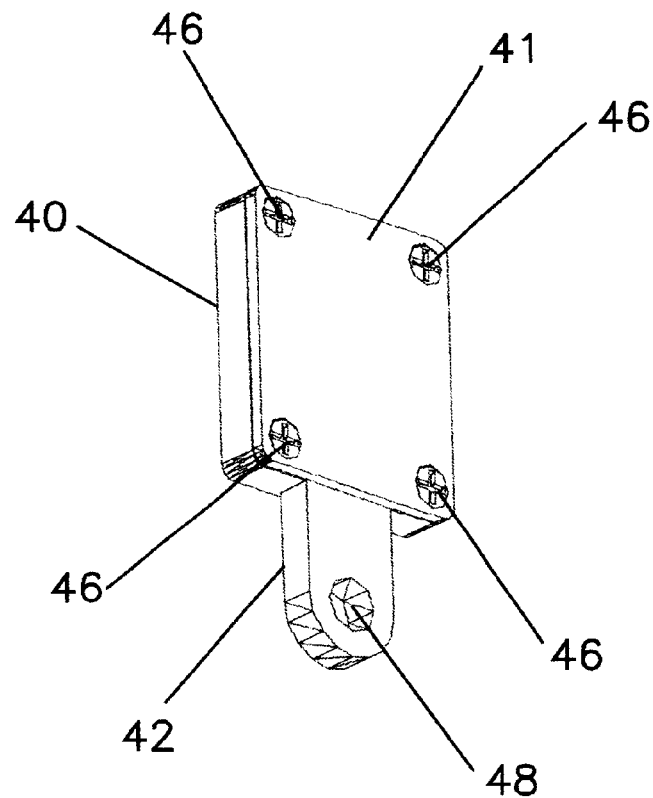
FIG. 2 is a frontal perspective of the lateral or medial mechanical joint.
Figure 3:
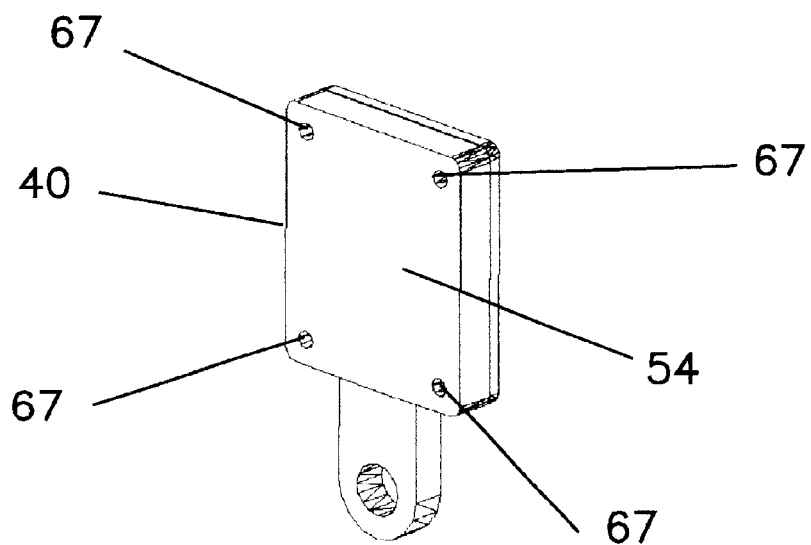
FIG. 3 is a rear perspective of the lateral or medial mechanical joint.
Figure 4:
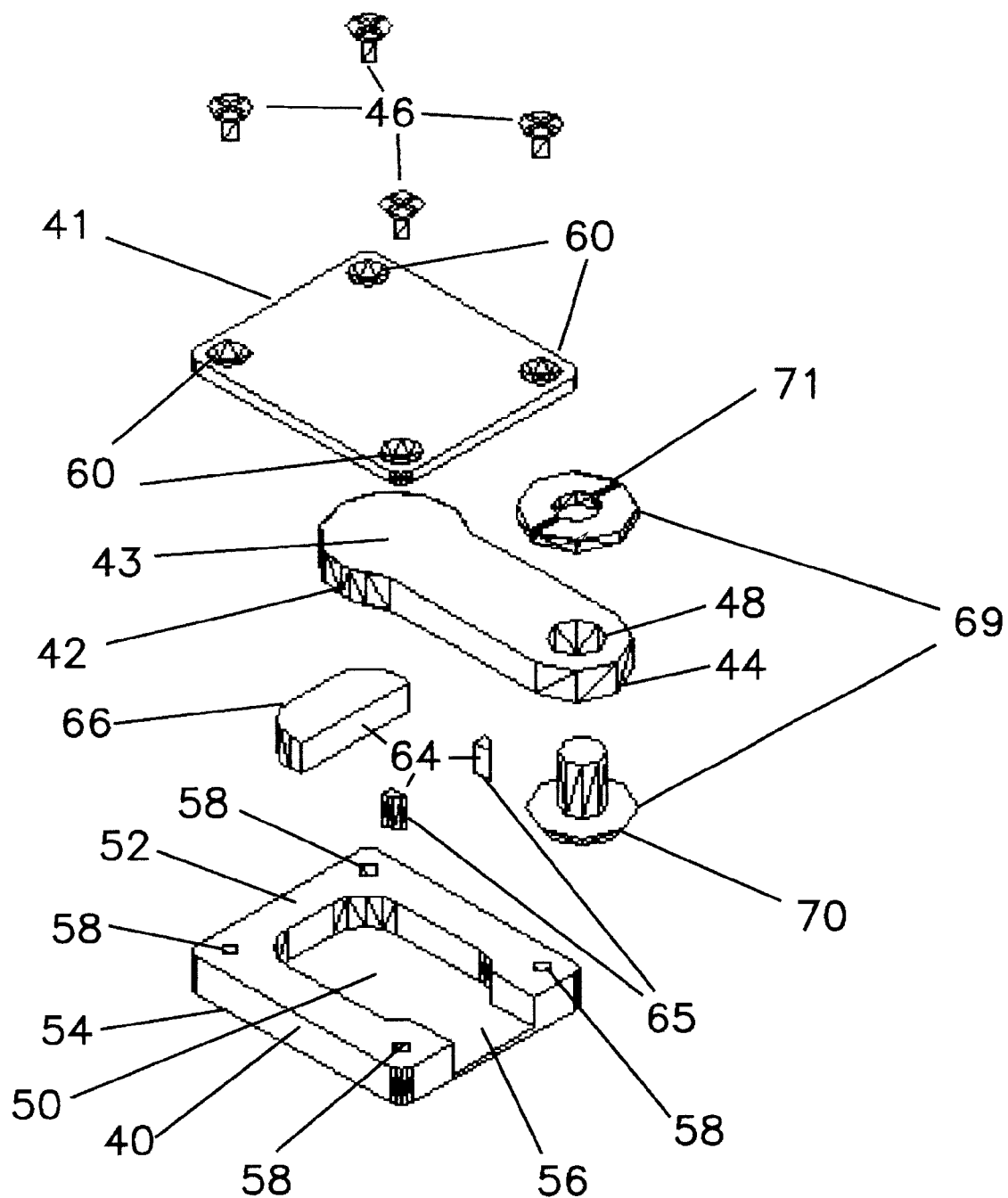
FIG. 4 is an exploded view of the lateral or medial mechanical joint.

Referring still to FIG. 1 and also to FIG. 2, FIG. 3 and FIG. 4, the hinging means 13 is comprised of a lateral mechanical joint 14 and a medial mechanical joint 16. The lateral mechanical joint 14 and the medial mechanical joint 16 are identical in design and in function and act together to pivotally attach the foot shell 10 to the lower leg shell 12, providing rotational and translational movement while restricting sideways bending movement of the ankle. The lateral mechanical joint 14 and the medial mechanical joint 16 are each comprised of a housing 40, a slider 42, a spring means 64 a cover 41 and a pivoting means 69.

The hinging means 13 pivotally connects the foot shell 10 to the lower leg shell 12 by being fixedly connected to the upper leg shell 12 and rotationally connected to the foot shell 10. The solid face 54 of the lateral mechanical joint 14 is secured to the inner surface 12*a* of the lower leg shell 12 at the lateral splay 31, above the ankle joint, using screws 62 threaded into holes 67 of the housing 40 in a manner whereby the slider 42 is vertically in line with the wearer's lower leg. At the same time, the solid face 54 of the medial mechanical joint 16 is secured to the inner surface 12*a* of the lower leg shell 12 at the medial splay 33, above the ankle joint, using screws 62 threaded into holes 67 of the housing 40 in a manner whereby the slider 42 is vertically in line with the wearer's lower leg. The lateral mechanical joint 14 and the medial mechanical joint 16 are also rotationally connected to the foot shell 10 each by said pivoting means 69, which comprises a bolt 70 and a retaining nut 71, on the internal surface 10*a* at the lateral flare 23 and at the medial flare 25, respectively. Bolt 70 is threaded and inserted through hole 48 of the slider 42 of the lateral mechanical joint 14 and the lateral flare 23 while a second bolt 70 is threaded and inserted through hole 48 of the slider 42 of the medial mechanical joint 16 and the medial flare 25, in each case the bolt 70 being secured in place by the retaining nut 71 threaded onto the bolt 70, each mechanical joint at a position at, and in line with, the axis of the ankle joint, thereby permitting rotation at the ankle joint.

Referring to FIG. 1, FIG. 2, FIG. 3 and FIG. 4, the housing 40 is made of a lightweight and strong material, such as aluminum, and comprises a hollow interior 50, an open face 52 that is open to the hollow interior 50, a solid face 54 that is 180° opposite to the open face 52 and a partially open end 56 that is at 90° to the open face 52 open to the hollow interior 50. The open face 52 has a threaded hole 58 defined at each corner sized to accept a screw 46. The solid face 54 has a threaded hole 67 defined near each corner to accept a screw 62.

The slider 42 is likewise made of lightweight strong material, such as aluminum, and comprises an upper end 43 and a lower end 44. The upper end 43 is positioned freely inside of the hollow interior 50 of the housing 40 while the lower end 44 projects out through an opening 100 of the partially open end 56. The slider 42 is rigidly constructed and is the same thickness as the depth of the hollow interior 50. The upper end 43 is round in shape and fits tightly inside of the hollow interior 50 of the housing 40. The upper end 43 is larger than the opening 100 of the partially open end 56 preventing the slider 42 from being removed through the partially open end 56. The lower end 44 is configured to fit with very little clearance though the partially open end 56. The combination of the shape of the slider 42 and the shape of the hollow interior 50 and the partially open end 56 of the housing 40 allows the slider 42 to move in only one direction inside of the housing 40, which is in line vertically with the lower leg when the hinging means 13 connects the foot brace 10 to the lower leg brace 12. The tight fit of the slider 42 in the hollow interior 50 and the partially open end 56 acts to keep the slider 42 from moving perpendicular to the lower leg in an axis forward and backward in line with the foot, while a cover 41, that is attached over the open face 52 of the housing 40, and flush to the slider 42, by means of screws 46 through countersunk holes 60 in the cover 41 and into holes 58 in the open face .52, prevent the slider 42 from moving in an axis perpendicular, side to side, against the ankle joint. The slider 42 also has a hole 48 defined through its lower end 44 to receive the pivoting means 69. Translational movement of the slider 42 in the housing 40 is thereby permitted while sideways bending movement is restricted.

The spring means 64 is located above and below the upper end 43 of the slider 42 inside of the housing 40. The spring means is comprised of a flexible and elastic rubber material freely positioned inside of the housing 40. An upper piece of rubber spring 66 is placed above the upper end 43 of the slider 42. A lower piece of rubber spring 65 is placed beneath the upper end 43 of the slider 42 adjacent to each side of the lower end 44 of the slider 42 and above and next to the partially open end 56 of the housing 40. The cover 41 will act to retain the spring means 64 inside of the housing 40.

Figure 6:
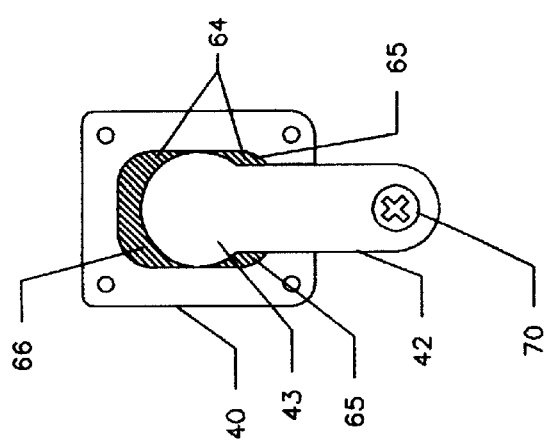
FIG. 6 is a cut away frontal view of the lateral or medial mechanical joint showing the lateral or medial mechanical joint in its neutral position at equilibrium, when no forces are applied to the ankle-foot orthotic.

Referring to FIG. 6, the mechanical joint is in a state of equilibrium. No forces in tension or compression are being applied to the mechanical joint and thereby no forces are being applied to the spring means 64 which displays no deformity.

Figure 5:
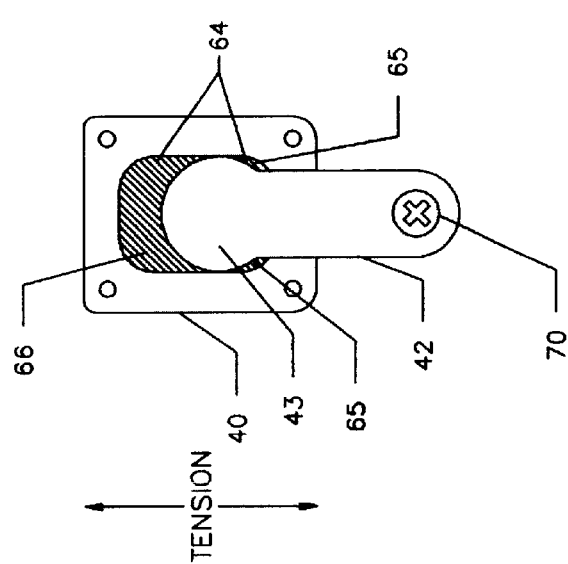
FIG. 5 is a cut away frontal view of the lateral or medial mechanical joint showing upward translational movement allowed by the lateral or medial mechanical joint when downward force, or tension, is applied to the ankle-foot orthotic.

FIG. 5 shows tension being applied to the mechanical joint and the resulting deformity to the spring means 64. The lower pieces of rubber spring 65 are being compressed by the slider 42 during this tension but act to absorb the shock of the tension and will return the slider 42 and the mechanical joint to a state of equilibrium when the tension is removed from the system.

Figure 7:
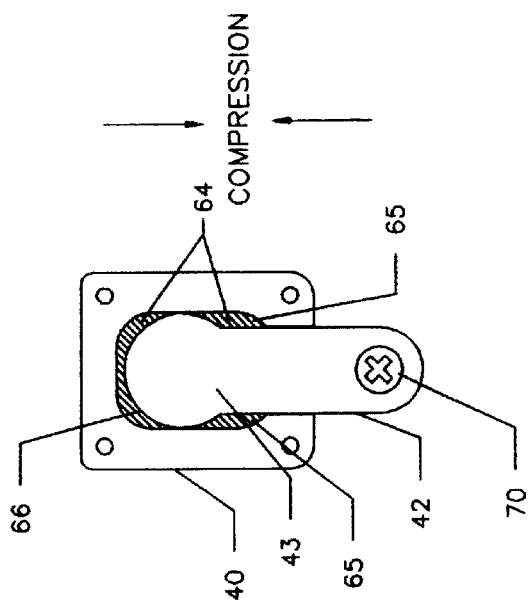
FIG. 7 is a cut away frontal view of the lateral or medial mechanical joint showing downward translational movement allowed by the lateral or medial mechanical joint when upward force, or compression is applied to the ankle-foot orthotic.

In FIG. 7, the mechanical joint is being subjected to compressive forces. As a result the upper piece of rubber spring 66 is being compressed by the slider 42. The upper piece of rubber spring 66 will act to cushion the shock of the compressive forces on the mechanical joint and will return the slider and the mechanical joint to a state of equilibrium when the compressive forces are removed from the system.

As shown in FIG. 1, FIG. 5, FIG. 6 and FIG. 7, the spring means 64 cushions and absorbs shock to the foot and ankle in up and down movement relative to the lower leg. The spring means also will return the ankle-foot orthotic 9 to a neutral position when forces in tension and compression are removed. Wearer comfort is improved by this cushioning but also further augmented since the hinging means 13 allows up and down movement along the axis of the lower leg of the foot shell 10 relative to the lower leg shell 12, meaning the foot and foot shell 10 can move up and down but the lower leg shell 12 can stay in position around the lower leg. This will decrease rubbing of the lower leg shell 12 on the lower leg of the wearer, thereby increasing comfort.

Working together, the lateral mechanical joint 14 and the medial mechanical joint 16 provide full rotational movement for the ankle-foot orthotic 9 and consequently plantarflexion and dorsiflexion to the wearer's foot and ankle in an axis through the ankle. Sideways bending movement of the foot shell 10 and lower leg shell 12 relative to each other is restricted by the lateral mechanical joint 14 and the medial mechanical joint 16 working together, thereby restricting inversion and eversion of the foot. The translational, up and down movement, permitted by the hinging means 13 allows some sideways bending movement of the lower leg shell 12 relative to the foot shell 10 but such movement is limited and can be limited further by shortening the travel of the slider 42 in the housing 40 or by shortening the lower end 44 of the slider 42 itself.

It will be apparent from the above that the ankle-foot orthotic of the present invention provides a simple, strong, versatile, lightweight and inexpensive ankle-foot orthotic that can easily be worn on the inside of the shoe and trousers of the wearer, with all the inherent advantages of an inside orthotic described above. Moreover, this simple and inexpensive brace readily permits normal rotational and translational movement of the foot an ankle, while at the same time carefully restricting and controlling excessive turning movement, inversion and eversion, of the foot. The wearer thereby will be able to participate in athletic activities or merely walk or recuperate from an ankle sprain in comfort and confidence that a new or further ankle sprain will not occur. The wearer will not only have support and comfort, but also will not suffer from the embarrassment or self-consciousness of a bulky outside ankle brace. The present invention can be custom fitted to any wearer for either foot and adjusted to the comfort and physical needs of said wearer.

It should be readily understood by persons skillful in the art that the present invention is susceptible to a broad utility and application. While we have described the preferred embodiment of the invention, other embodiments and modifications could be implemented without departing from the spirit of the invention and from the scope of the appended claims. The foregoing disclosure is thus not intended to limit the present invention or otherwise to exclude any other such equivalent embodiments, adaptations, variations or modifications, the present invention being limited only by the claims appended hereto and the equivalents thereof.

I claim:

1. An ankle-foot orthotic for restricting inversion and eversion of the foot while allowing plantarflexion and dorsiflexion of the foot and permitting translational movement of said ankle-foot orthotic comprising:

a foot shell;

a lower leg shell; and a hinging means pivotally attaching said foot shell to said lower leg shell, said hinging means providing rotational and translational movement to, and restricting sideways bending movement of, said foot shell relative to said lower leg shell, said hinging means comprising a lateral mechanical joint and a medial mechanical joint, said lateral mechanical joint and said medial mechanical joint each comprising:

a housing, said housing including a hollow interior, an open face, a solid face and a partially open end, said partially open end having an opening through said partially open end;

a slider having an upper end and a lower end, said slider being rigid, said slider being positioned freely inside of said hollow interior of said housing, said lower end of said slider projecting through and outside of said opening of said partially open end of said housing, said upper end of said slider being larger than said opening of said open end of said housing but smaller than said hollow interior of said housing allowing translational movement of said slider inside of said hollow interior of said housing while restricting sideways movement of said slider inside of said hollow interior of said housing and preventing removal of said slider through said opening of said partially open end of said housing;

a cover affixed to said open face of said housing;

a spring means placed inside of said hollow interior of said housing, said spring means providing cushioning for said slider while allowing said slider to return to a neutral position inside of said hollow interior of said housing; and a pivoting means attached to said lower end of said slider.

2. The ankle-foot orthotic as recited in claim 1 wherein said spring means comprises elastic rubber material positioned snugly above and below said upper end of said slider inside of said hollow interior of said housing.

3. The ankle-foot orthotic as recited in claim 1 wherein said foot shell is composed of a plastic material moldable to the shape of a user's foot, the plastic material defining an internal surface and an external surface, designed to fit inside of a user's shoe and be secured to the user's foot by the user's shoe, said foot shell comprising:

a lower plate;

an upright lateral sidewall, said upright lateral sidewall being sized and configured to flare away from a user's ankle during use, providing clearance for the user's ankle and clearance for positioning and attachment of said lower end of said slider of said lateral mechanical joint to said upright lateral sidewall;

an upright medial sidewall, said upright medial sidewall being sized and configured to flare away from the user's ankle during use, providing clearance for the user's ankle and clearance for positioning and attachment of said lower end of said slider of said medial mechanical joint to said upright medial sidewall; and a rounded posterior wall.

4. The ankle-foot orthotic as recited in claim 1 wherein said lower leg shell is composed of a plastic material moldable to the shape of a user's lower leg, the plastic material defining an inner surface and an outer surface, said lower leg shell comprising:

a vertical lateral sidewall having a lateral top end and a lateral bottom end, said lateral bottom and being sized and configured to splay away from a user's ankle during use, providing clearance for the user's ankle and clearance for positioning and attachment of said solid face of said housing of said lateral mechanical joint;

a vertical medial sidewall having a medial top end and a medial bottom end, said medial bottom end being sized and configured to splay away from the user's ankle during use, providing clearance for the user's ankle and clearance for positioning and attachment of said solid face of said housing of said medial mechanical joint;

a vertical rounded posterior wall having a posterior top end and a posterior bottom end;

a means to secure said lower leg shell to the user's lower leg; and a gap defined between said vertical lateral sidewall and said vertical medial sidewall opposite said rounded posterior wall allowing insertion of the user's lower leg during use.

5. The ankle-foot orthotic as recited in claim 3 wherein said pivoting means comprises:
- a first bolt passing through said lower end of said slider of said lateral mechanical joint and through said upright lateral sidewall of said foot shell;
- a second bolt passing through said lower end of said slider of said medial mechanical joint and through said upright medial sidewall of said foot shell; and
- a first retaining nut threaded onto said first bolt and a second retaining nut threaded onto said second bolt, thereby pivotally securing said slider, laterally and medially, to said foot shell allowing rotational movement between said foot shell and said lower leg shell.

6. The ankle-foot orthotic as recited in claim 4 wherein said solid face of said housing of said lateral mechanical joint is affixed to said inner surface of said lateral bottom end of said vertical lateral sidewall of said lower leg shell with a plurality of screws; and said solid face of said housing of said medial mechanical joint is affixed to said inner surface of said medial bottom end of said vertical medial sidewall of said lower leg shell with a second plurality of screws.

* * * * *